(12) United States Patent
Mirle et al.

(10) Patent No.: US 8,101,814 B2
(45) Date of Patent: Jan. 24, 2012

(54) BREATHABLE ABSORBENT ARTICLES AND COMPOSITES COMPRISING A VAPOR PERMEABLE, LIQUID BARRIER LAYER

(75) Inventors: Srinivas Krishnaswamy Mirle, Liberty Township, OH (US); Angelli Sue Denmon, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 61 days.

(21) Appl. No.: 10/844,182

(22) Filed: May 12, 2004

(65) Prior Publication Data

US 2005/0256476 A1    Nov. 17, 2005

(51) Int. Cl.
*A61F 13/15* (2006.01)
*A61F 13/20* (2006.01)

(52) U.S. Cl. .................. 604/382; 604/378; 604/367

(58) Field of Classification Search .................. 604/367, 604/370, 372, 374–379, 385.01, 381–382
See application file for complete search history.

(56) References Cited

U.S. PATENT DOCUMENTS

| 5,628,737 | A * | 5/1997 | Dobrin et al. ................. 604/383 |
| 6,153,209 | A * | 11/2000 | Vega et al. .................... 424/404 |
| H1969 | H | 6/2001 | Fell et al. |
| H1978 | H | 8/2001 | Freiburger et al. |
| H2011 | H | 1/2002 | Freiburger et al. |
| 6,369,292 | B1 * | 4/2002 | Strack et al. ................. 604/370 |
| 2003/0065298 | A1 | 4/2003 | Krishnaswamy-Mirle et al. |

FOREIGN PATENT DOCUMENTS

| EP | 0 868 895 B1 | 3/2003 |
| WO | WO 96/25902 A1 | 8/1996 |
| WO | WO 01/00120 A1 | 1/2001 |
| WO | WO 01/00121 A1 | 1/2001 |
| WO | WO 01/05346 A1 | 1/2001 |
| WO | WO 01/22908 A1 | 4/2001 |
| WO | WO 01/82849 A1 | 11/2001 |
| WO | WO 01/82851 A1 | 11/2001 |
| WO | WO 01/91685 A1 | 12/2001 |

\* cited by examiner

*Primary Examiner* — Michele M Kidwell
(74) *Attorney, Agent, or Firm* — Dara M. Kendall; John P. Colbert; William E. Gallagher

(57) ABSTRACT

The present invention relates to absorbent articles and composites that provide improved protection and comfort by use of a vapor permeable, liquid barrier layer. In particular, this layer results from deposition of barrier coating on one or more regions of the barrier layer such that select regions of the overall article exhibit a barrier to liquid while the article in general is still deemed breathable.

17 Claims, 3 Drawing Sheets

BREATHABLE ABSORBENT ARTICLES AND COMPOSITES COMPRISING A VAPOR PERMEABLE, LIQUID BARRIER LAYER

FIELD OF INVENTION

The present invention relates to absorbent articles and composites that each include a barrier layer which helps to provide 1) improved protection against wetness strikethrough that typically results from impact or sustained pressure, 2) improved dampness management character, and 3) high convective vapor flow through for skin health and comfort benefits.

BACKGROUND OF THE INVENTION

Many known absorbent articles such as diapers, incontinence articles, feminine hygiene products, and training pants, typically comprise absorbent core materials located between a liquid pervious bodyside liner or topsheet and a vapor permeable, liquid impermeable backsheet. The bodyside liner allows bodily liquids to flow through easily towards the absorbent core. The absorbent core takes up the liquids quickly. Thus, no excessive pooling of liquids occurs on the body-facing surface of the absorbent article. The outer cover is typically liquid impermeable such that there is no leakage from the absorbent article. Since, however, the disposable absorbent article may be worn for hours after coming in contact with body exudates and perspiration from the wearer's body, liquid vapors escaping from the absorbent core often get entrapped in the space between the absorbent article and the wearer's skin, resulting in an increased relative humidity in the occluded area. As is known in the art, the increased relative humidity leads to discomfort and overhydrated skin that is prone to skin health problems, especially rashes and other contact dermatitis.

Such backsheets are well suited to prevent the leakage of bodily fluids (such as urine, menses or fecal matter) from the absorbent material to the outer garment of a wearer. Unfortunately, the use of such an impermeable backsheet can result in a high degree of humidity in the absorbent article when the absorbent article is in use such that relatively elevated skin hydration levels may result.

Attempts at remedying this problem have included utilizing microporous or monolithic films as backsheet materials which then allow air and water vapor diffusion. Others have tried incorporating high permeability zones within the absorbent core, such as by aperturing the absorbent core or by creating portions in the core containing substantially less high absorbency materials than in other portions of the core. Absorbent articles relying on these technologies have still tended to exhibit significantly increased relative humidity between the skin of the wearer and the article when the article is loaded with liquids.

One phenomenon of particular interest that affects a loaded or wet absorbent article is any pressure or impact force due to the wearer's motion, such as sitting, walking, bending, and falling. Known absorbent articles still tend to fail to hold liquids when they are loaded to their absorbent capacity especially when the loaded absorbent article is under pressure or impact due to a wearer's motion.

It has been observed by the Applicants that convective vapor flow is much more effective than diffusive vapor flow when there is a damp absorbent article core present. Consequently, there is a need for absorbent articles which deliver a combination of benefits to the wearer. These benefits should include an improved liquid impact capability, breathability (i.e., air vapor flow via convection), water vapor transmission (i.e., through diffusion) and resistance to leakage under impact or sustained pressure.

SUMMARY OF THE INVENTION

The present invention relates to a disposable absorbent article comprising:
a. a liquid permeable topsheet;
b. a liquid impervious outer cover;
c. an absorbent core disposed between said topsheet and outer cover, wherein said core comprises a first and second region; and
d. a barrier layer disposed either between said topsheet and core or between said core and outer cover, wherein said barrier layer comprises:
1) a first region;
2) a second region disposed adjacent said first region of said barrier layer; and
3) a barrier coating disposed onto one or more surfaces of said first region of said barrier layer; wherein said barrier coating inhibits the flow of a liquid in the first region of said barrier layer as compared to the flow of the liquid in the second region of said barrier layer; and
wherein said first region of said barrier layer exhibits a water vapor transmission rate (WVTR) of from about 100 to about 50,000 gsm/day and a convective air permeability of at least about 0.01 cfm.

In another embodiment, the present invention relates to a disposable composite that comprises:
a. a first region;
b. a second region;
c. a barrier coating disposed onto one or more surfaces of said first region of said barrier layer; wherein said barrier coating inhibits the flow of a liquid in the first region of said barrier layer as compared to the flow of the liquid in the second region of said barrier layer; and
wherein said first region of said barrier layer exhibits a water vapor transmission rate (WVTR) of from about 100 to about 50000 gsm/day and a convective air permeability of at least about 0.01 cfm.

DETAILED DESCRIPTION OF THE INVENTION

Definitions

Figure 1:
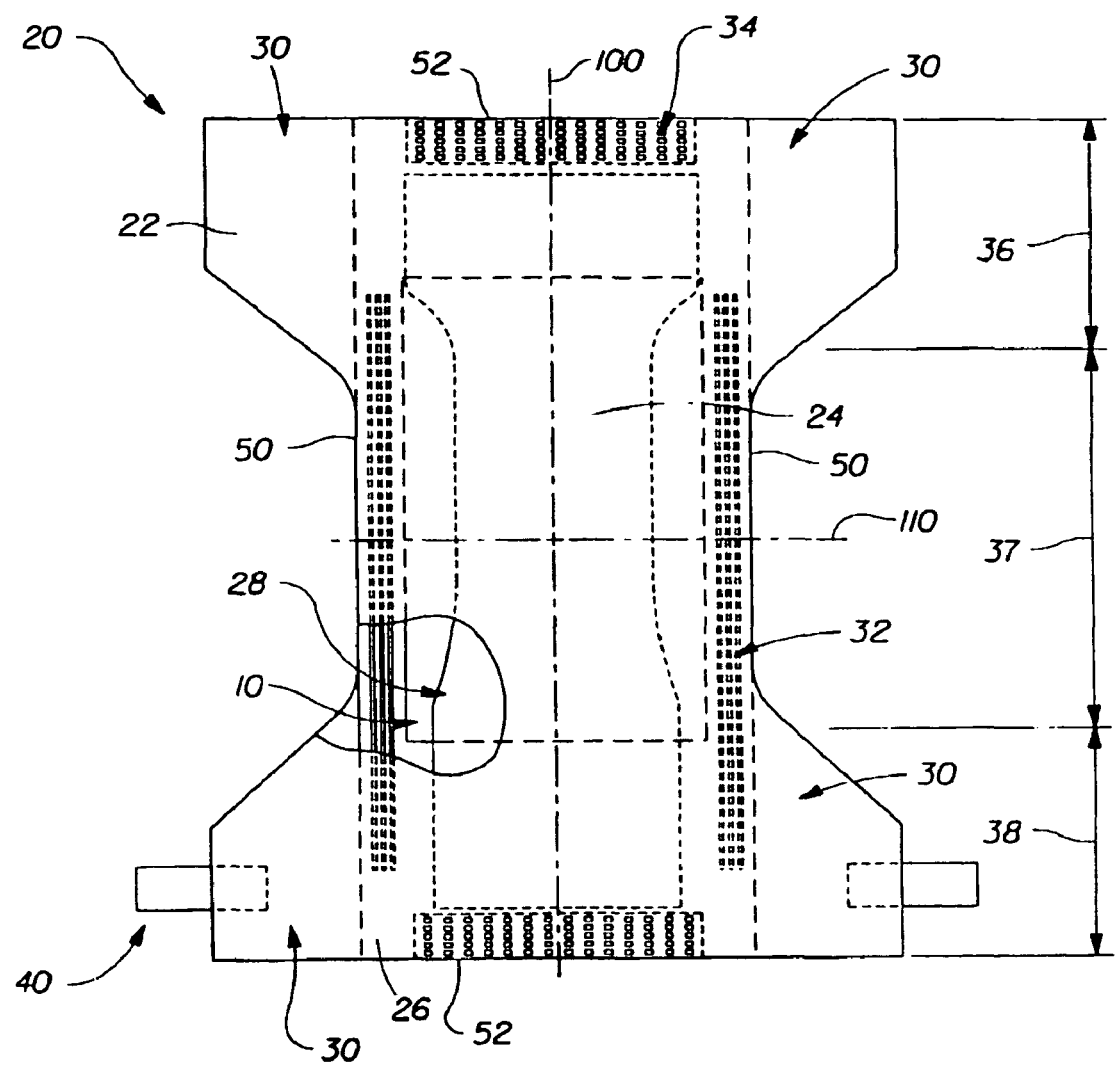
FIG. 1 is a partially broken top plan view of an absorbent article of the present invention which includes a barrier layer.

As used herein, the term "absorbent articles" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates"

includes, but is not limited to, urine, blood, vaginal discharges, breast milk, sweat and fecal matter.

As used herein, the term "absorbent core" refers to the component of the absorbent article that is primarily responsible for fluid handling properties of the article, including acquiring, transporting, distributing and storing body fluids. As such, the absorbent core typically does not include the topsheet, backsheet or outer cover of the absorbent article.

As used herein, the term "bonded" refers to different materials being attached (cohesively or adhesively) in at least a portion thereof. The attached portions may be random or may have a pattern such as stripes, spirals, dots, and the like. The attached portions may be located at the peripheries, throughout the surface area, or both. Suitable attachment means known in the art may be used, including but not limited to adhesives, heat, pressure, crimping, ultrasonic, chemical (via hydrogen bonds or other cohesive forces), mechanical (e.g., fasteners, entanglements), hydraulic, vacuum and combinations thereof.

As used herein, the term "composite structure" refers to a multi-region structure wherein the materials comprising the regions may be operatively associated or bonded. The regions may even be in intimate contact such that the composite has a unitary structure. Further, the regions may be positioned in a layered (face-to-face) arrangement, or a side-by-side arrangement.

As used herein, the term "disposable" is used in its ordinary sense to mean an article that is disposed or discarded after a limited number of usage events over varying lengths of time, preferably less than about 20 events, more preferably less than about 10 events, even more preferably less than about 5 events, and most preferably less than about 2 events.

As used herein, the term "joined" encompasses configurations wherein an element is directly secured to the other element by affixing the element directly to the other element, and configurations wherein the element is indirectly secured to the other element by affixing the element to intermediate member(s), which in turn are affixed to the other element.

The term "macroporous" refers to materials having pores too large to effect capillary transport of fluid, generally having pores greater than about 0.5 mm in diameter and, more specifically, having pores greater than about 1.0 mm in diameter.

As used herein, the terms "meltblown" and "meltblown web" refer to a web having fibers formed by extruding a molten thermoplastic material through a plurality of fine, usually circular, die capillaries as molten threads or filaments into converging high velocity heated gas/air streams which attenuate the molten filaments to reduce their diameter. The reduction in fiber diameter is substantially greater then the reduction of fiber diameter in the spunbonding process, resulting in microfibers having average fiber diameter larger than 0.2 microns and typically in the range of 0.6 to 10 microns. Thereafter, the meltblown fibers are carried by the high velocity gas stream and are deposited on a collecting surface to form a web of randomly disbursed fibers. Various melt blown processes are known in the art.

As used herein, the term "microporous" refers to materials which are capable of transporting fluids through relatively small pores that possess tortuous paths.

As used herein, the terms "nonwoven" and "nonwoven web" refers to a web that has a structure of individual fibers which are interlaid forming a matrix, but not in an identifiable repeating manner. Nonwoven webs may be formed by a variety of processes known to those skilled in the art, for example, meltblowing, spunbonding, wet-laying, air-laying, and various bonding-carding processes.

As used herein, the term "operatively associated" refers to a structure comprising different materials positioned at least in partial contact with each other in use. The materials are physically separable and each exhibits properties that can be measured individually. The materials may be arranged in a face-to-face relationship in the z-dimension, or in a side-by-side relationship in the xy-dimension.

As used herein, the term "pulp" or "cellulosic fibers" include those natural fiber derived from trees or vegetations (e.g., hardwood fibers, softwood fibers, hemp, cotton, flax, esparto grass, milkweed, straw, bagasse and the like), their processed/regenerated fibers (e.g., Rayon®) or chemically derivatized fibers (e.g., cellulose esters), and combinations thereof. Suitable hardwood fibers include eucalyptus fibers. Suitable hardwood fibers may be prepared by kraft or other chemical pulping methods. Suitable softwood fibers include southern softwood (SS) fibers and northern softwood (NS) fibers. Softwood fibers for use herein can be chemically (e.g., without limitation, kraft pulp) or mechanically pulped (e.g., without limitation, chemithermal mechanical pulp (CTMP) and thermal mechanical pulp (TMP)).

As used herein, the term "region" refers to a zone or an area comprising a material being physically, chemically, or visually distinguishable from surrounding or adjoining materials. Various regions of materials may include transitional regions in between. The regions may be positioned in the z-dimension or in the xy-dimension. As used herein, the term "z-dimension" refers to the dimension orthogonal to the length and width of the structure or article. The z-dimension usually corresponds to the thickness of the structure or article. As used herein, the term "xy-dimension" refers to the plane orthogonal to the thickness of the member, core or article when the member, core or article is in a flat-out state. The xy-dimension usually corresponds to the length and width, respectively, of the structure or article in a flat-out state.

As used herein, the terms "spunbond" and "spunbonded web" refers to a web having fibers formed by extruding a molten thermoplastic material as filaments from a plurality of fine capillaries of a spinnerette having a circular or other configuration, then rapidly reducing the diameter of the extruded filaments by fluid drawing or other well known spunbonding mechanisms. Spunbond fibers are quenched and generally not tacky when they are deposited onto a collecting surface. Spunbond fibers are generally continuous and often have average between about 10 to about 30 microns.

As used herein, the term "unitary structure" refers to a structure comprising materials having different characteristics joined together to form an integral entity such that the materials are substantially inseparable physically, and the unitary structure exhibits properties resulting from the combination of the materials therein. The materials may be arranged in a face-to-face relationship in the z-dimension, or in a side-by-side relationship in the xy-dimension.

The following detailed description is directed toward absorbent articles. It is, however, likely that the disclosed articles could be modified such that the overall concept discussed herein could likewise be applied to use in other hygiene or health care products, such as bandages, dressings, wipes, bibs, surgical drapes, surgical gowns, and the like.

Absorbent Article Components

FIG. 1 is a partially broken top plan view of a particular absorbent article of the present invention. This article is a diaper 20 containing the barrier layer 10 of the present invention. The diaper 20 is in a flat-out state with portions of the structure cut away to more clearly show the construction of the diaper 20. The garment-facing surface of the diaper 20 is oriented away from the viewer.

As shown in FIG. 1, the diaper 20 comprises a liquid pervious topsheet 24; an absorbent core 28, which is positioned between at least a portion of the topsheet 24 and the outer cover 22; a barrier layer 10 positioned between the absorbent core 28 and the outer cover 22; side panels 30; elasticized leg cuffs 32; elastic waist features 34; and a fastening system 40.

Diaper 20 is shown in FIG. 1 to have a front waist region 36, a rear waist region 38 opposed to the front waist region 36 and a crotch region 37 located between the front and the rear waist regions. The peripheries of the diaper 20 are defined by the outer edges of the diaper 20 in which the longitudinal edges 50 run generally parallel to the longitudinal centerline 100 of the diaper 20 and end edges 52 run between the longitudinal edges 50 generally parallel to the lateral centerline 110 of the diaper 20.

The main body of the diaper 20 comprises at least the absorbent core 28, and the topsheet 24. An outer cover 22 forms the chassis, onto which other components of the diaper 20 are added to form the unitary structure of the diaper.

FIG. 1 shows an embodiment of the diaper 20 in which the topsheet 24 has length and width dimensions generally no smaller than those of the absorbent core 28 and the barrier layer 10. The topsheet 24 may extend to the peripheries of the diaper 20. In another embodiment, the barrier layer 10 may extend beyond the edges of the absorbent core 28 to the peripheries or edges of the diaper 20.

While the components of the diaper 20 may be assembled in various well known configurations, preferred diaper configurations are described generally in U.S. Pat. Nos. 3,860,003, 5,151,092, 5,221,274, 5,554,145, 5,569,234, 5,580,411, and 6,004,306.

In alternative embodiments, the article may be preformed by the manufacturer to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433; 5,569,234, 6,120,487, 6,120,489, 4,940,464, 5,092,861, 5,897,545, 5,957,908, and U.S. Patent Publication 2003/0233082A1.

Topsheet

The topsheet is compliant, soft feeling, and non-irritating to the wearer's skin. The topsheet material can also be elastically stretchable in one or two directions. Further, the topsheet is fluid pervious, permitting fluids (e.g., urine, menses, other bodily fluids) to readily penetrate through its thickness. A suitable topsheet can be manufactured from a wide range of materials such as woven and nonwoven materials; apertured or hydroformed thermoplastic films; porous foams; reticulated foams; reticulated thermoplastic films; and thermoplastic scrims. Suitable woven and nonwoven materials may comprise of natural fibers such as wood or cotton fibers; synthetic fibers such as polyester, polypropylene, or polyethylene fibers; or combinations thereof. If the topsheet includes fibers, the fibers may be spunbond, carded, wet-laid, meltblown, hydroentangled, or otherwise processed as is known in the art. One suitable topsheet comprising a web of staple-length polypropylene fibers is manufactured by BBA Nonwovens of Old Hickory, Tenn. and us available under the designation P-8.

Preferred topsheet for use in the present invention are selected from high loft nonwoven topsheets and apertured film topsheet. Apertured film topsheet typically are pervious to bodily exudates, yet non-absorbent, and have a reduced tendency to allow fluids to pass back through and rewet the wearer's skin. Suitable apertured films include those described in U.S. Pat. No. 5,628,097, U.S. Pat. No. 5,916,661, WO 00/69382 A2, U.S. Pat. No. 6,545,197, and U.S. Pat. No. 6,107,539.

Further, suitable topsheet materials for depositing solid excretions thereon may include nonwovens having apertures, which are at least in the portions that are aligned with the feces deposition region of the article. Suitable apertured nonwovens are described in more detail in U.S. Pat. Nos. 6,414,215, 5,342,338, and 5,941,864 and U.S. Patent Publication 2002/017376. In another embodiment of feces handling articles, such topsheets can be combined with feces handling members, e.g., underlying such topsheets, and which are further described in the abovementioned patent documents.

Suitable formed film topsheets are described in U.S. Pat. Nos. 3,929,135, 4,324,246, 4,342,314, 4,463,045, 5,006,394. Other suitable topsheets may be made in accordance with U.S. Pat. Nos. 4,609,518 and 4,629,643. Such formed films are available as "DRI-WEAVE" and "CLIFF-T" and are available from Tredegar Corporation, based in Richmond, Va.

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and/or immersing the material into the surfactant. A more detailed discussion of such a treatment and hydrophilicity is contained in U.S. Pat. Nos. 4,988,344, 4,988,345, and 4950254. A more detailed discussion of some suitable methods for incorporating a surfactant in the topsheet 24 can be found in U.S. Statutory Invention Registration No. H1670 published on Jul. 1, 1997 in the names of Aziz et al. Alternatively, the topsheet 24 may include an apertured web or film which is hydrophobic. This may be accomplished by eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. Nos. 5,607,760, 5,609,587, 5,635,191, 5,643,588, and 5,968,025. The lotion may function alone or in combination with another agent as the hydrophobizing treatment described above. The topsheet may also include or be treated with antibacterial agents, some examples of which are disclosed in PCT Publication No. WO 95/24173. Further, the topsheet, the outer cover or any portion of the topsheet or outer cover may be embossed and/or matte finished to provide a more cloth like appearance.

The topsheet may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" (from the article) is increased. Typically, the aperture should have an area of between about 10 cm$^2$ and about 50 cm$^2$. The aperture preferably has an area of between about 15 cm$^2$ and 35 cm$^2$.

Further, the topsheet may be fully or partially elasticated or may be foreshortened so as to provide a void space between the topsheet and the core. Exemplary structures including elasticized or foreshortened topsheets are described in more detail in U.S. Pat. Nos. 4,892,536, 4,990,147, 5037416; and 5269775.

Absorbent Core

The absorbent core may take on any size or shape that is compatible with the diaper. One preferred embodiment of the diaper has an asymmetric, modified T-shaped absorbent core having ears in the first waist region but a generally rectangular shape in the second waist region. Exemplary absorbent structures for use as the absorbent core of the present invention that have achieved wide acceptance and commercial success are described in U.S. Pat. Nos. 4,610,678, 4,673,402, 4,888,231, 4,834,735, 5,137,537, 5,147,345, 5,342,338, 5,260,345, 5,387,207, 5,234,423, and 5,625,222.

The absorbent core typically comprises absorbent materials including absorbent gelling materials, which are usually referred to as "hydrogels", "superabsorbent", "hydrocolloid" materials. Absorbent gelling materials are those materials that, upon contact with aqueous fluids, such as bodily fluids, imbibes such fluids and form hydrogels. These absorbent gelling materials are typically capable of absorbing large quantities of aqueous bodily fluids, and further capable of retaining such absorbed fluids under moderate pressures. These absorbent gelling materials are typically in the form of discrete, nonfibrous particles. Other forms, such as fibers, foams, sheets, strips, or other macrostructures, are also suitable for use herein. Suitable absorbent gelling materials in the form of open cell foams may include those disclosed in U.S. Pat. Nos. 3,563,243, 4,554,297, 4,740,520, and 5260345.

The absorbent gelling materials suitable for use herein may comprise a substantially water-insoluble, slightly crosslinked, partially neutralized, polymeric gelling material. This material forms a hydrogel upon contact with water. Suitable absorbent gelling materials include those disclosed in U.S. Pat. Nos. 4,654,039, 5,562,646, 5,599,335, and 5,669,894.

Such absorbent gelling materials can be arranged in a homogeneous mixing with fluff pulp and/or synthetic fibers (as described herein), or can be layered between suitably open and permeable layers of porous materials, such as tissues, especially if these are air-laid, or nonwoven materials.

Particularly suitable materials are superabsorbent materials of U.S. Pat. No. 5,599,335, when arranged in a homogeneous blend with conventional fluff pulp, at a concentration of about 50% superabsorbent, preferably about 80% and even more preferably more than about 90% concentration based on the weight of the superabsorbent/fluff mixture. Suitable mixtures can further exhibit densities of between about 0.1 g/cm$^3$ and about 0.3 cm$^3$, preferably between about 0.15 cm$^3$ and about 0.2 cm$^3$.

In particular embodiments, such mixtures can comprise means which enhance the integrity of the mixture, especially in the dry state. Thus, low amounts of adhesive may be added to the mixture, or other binders, such as thermobondable synthetic fibers.

In addition to the liquid storage elements in the core, the core may comprise other liquid handling members, such as for enhancing fluid acquisition, or distribution.

Suitable carrier materials for inclusion into the core include cellulose fibers, in the form of fluff, tissues or paper. Modified cellulose fibers (e.g., stiffened, chemically treated, crosslinked) may also be used. Synthetic fibers may also be used. Suitable synthetic fibers may be made of cellulose acetate, polyvinyl fluoride, polyvinylidene chloride, acrylics (such as Orlon®), polyvinyl acetate, non-soluble polyvinyl alcohol, polyethylene, polypropylene, polyamides (such as Nylon®), polyesters, bi- or tri-component fibers thereof, and mixtures of these materials. Preferably, the fiber surfaces are hydrophilic or are treated to be hydrophilic.

Typically, the core comprises from about 15 to about 100 wt % of the absorbent gelling material dispersed in a carrier material. Preferably, the core comprises from about 30 to about 95 wt %, more preferably from about 60 to about 90 wt % of the absorbent gelling material. The carrier material typically comprises from about 0 to about 85 wt %, preferably from about 5 to about 70 wt %, and more preferably from about 10 to about 40 wt % of the storage layer.

In certain embodiments of the present invention, the absorbent article may also include a sublayer disposed between the topsheet and the outer cover. The sublayer may be any material or structure capable of accepting, storing or immobilizing bodily exudates. Thus, the sublayer may include a single material or a number of materials operatively associated with each other. Further, the sublayer may be integral with another element of the absorbent article or may be one or more separate elements joined directly or indirectly with one or more elements of the article. Further, the sublayer may include a structure that is separate from the core or may include or be part of at least a portion of the core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Outer Cover

The term "outer cover" as used herein means a structural element positioned on the garment-facing surface of the absorbent article. The outer cover typically forms the chassis onto which other components of the diaper are added. The outer cover, however, may just be a coating layer on the garment side of the absorbent article.

Suitable material for the outer cover should provide a nonwoven web that provides a garment-like fit character to the absorbent article as well as a structural support for the barrier layer and absorbent core. The outer cover should not be the rate limiting element to gas or vapor transport through the absorbent article. Preferably, the outer cover has a structure that is relatively open to allow for convective air or gas permeability. The suitable outer cover typically has a water vapor transmission rate (WVTR) of at least about 5000 gsm/day, more preferably of at least about 15,000 gsm/day, and most preferably at least about 30,000 gsm/day. Additionally, the outer cover provides a soft, pleasant feel to the skin, either by the material property, or by texturizing or embossing its surface, or both.

The outer cover may be a single layer of homogeneous or multi-component material, or a composite of various layers of materials. The outer cover suitable for use herein comprises porous materials such as an apertured film (e.g., having a plurality of shaped openings or angled capillaries), a knitted web, a porous woven or nonwoven web, a foam, or combinations or laminates thereof. In one embodiment, the outer cover comprises nonwoven webs or multi-layered nonwovens such as spunbond nonwoven (SB), spunbond/meltblown nonwoven (SB/MB), spunbond/meltblown/spunbond (SBS) nonwoven.

In certain embodiments, the outer cover may include a backsheet that is made of an apertured, thin plastic film such as a thermoplastic film having a thickness of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the absorbent article while still preventing exudates from passing through the backsheet. Some breathable composite materials are described in greater detail in U.S. Pat. Nos. 5,938,648, 5,865,823, and 5,571,096.

The outer cover, or any portion thereof, may be elastically extensible in one or more directions. In one embodiment, the outer cover may comprise a structural elastic-like film ("SELF") web. A SELF web is an extensible material that exhibits an elastic-like behavior in the direction of elongation without the use of added elastic materials and is described in more detail in U.S. Pat. No. 5,518,801. In alternate embodiments, the outer cover may combine elastomeric components (such as films, foams, strands, or combinations thereof) with nonwovens or synthetic films.

In another embodiment, the outer cover may be a nonwoven web constructed to provide the required level of liquid impermeability. For example, a nonwoven web of spunbonded or meltblown polymer fibers may be treated, at least partially, with a hydrophobic coating. Exemplary treatments using fluorocarbons are described in U.S. Pat. Nos. 5,876,753, 5,888,591, 6,045,877, and U.S. patent application Ser. No. 99/20504.

The absorbent article may comprise an outer cover that is separated from the absorbent core at least partially by the barrier layer and is preferably joined to the barrier layer and/or the absorbent core by attachment means such as those well known in the art.

The outer cover may be secured to the barrier layer, topsheet, absorbent core, or any other element of the absorbent article by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785,996, and 4,842,666. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The outer cover material should not significantly lower the convective air permeability of the absorbent article. More importantly, the combination of the barrier layer and the outer cover (hereinafter referred to as the "combined structure" or "combination") provide the desired balance of properties, including, but not limited to, barrier property and convective air permeability.

Barrier Layer

The absorbent articles of the present invention provide an improved barrier function against liquid or wetness strikethrough upon impact or continued application of pressure, even while maintaining a breathable character. This benefit is brought about by the inclusion of a barrier layer in the absorbent article. This barrier layer comprises a first region upon which a barrier coating is disposed and a second region onto which substantially no barrier coating is disposed. The barrier coating inhibits the flow of a liquid and/or water vapor in the first region of the barrier layer as compared to the flow of the liquid in the second region of the barrier layer such that the first region of this barrier layer exhibits a water vapor transmission rate (WVTR) of from about 100 to about 50,000 gsm/day and a convective air permeability of at least about 0.01 cfm. The barrier layer allows convective air or water vapor transport though the entire composite structure while minimizing the amount of actual liquid that can pass through the partially occluded (or coated) first region as compared to the second region of its barrier layer. Particularly, this layer of the presently claimed absorbent article and/or composite achieves the desirable convective air flow capacity without sacrificing the barrier protection against wet through. Thus, a barrier layer inclusive absorbent article shows effective reduction of the relative humidity in the space between the absorbent article and the wearer, thus, improves and/or maintains skin health and wearer comfort.

The barrier coating may be applied to the first region in a variety of manners including, but not limited to, dipping, brushing, coating, printing, slot-coating, powder coating, and combinations thereof. Preferably, though the barrier coating is applied via a mechanism selected from the group consisting of dipping, brushing, coating, printing, slot-coating, and combinations thereof.

The coated first region of the present invention may be constructed to have a convective air permeability of at least about 0.01 cfm, preferably at least about 0.05 cfm, and most preferably at least about 0.1 cfm. Convective air permeability is especially effective in removing water vapor from inside the absorbent article, resulting in a lower humidity in the local environment next to the skin, which reduces incidences of skin irritation or rash and promotes skin health. On the other hand, uncoated second region may be constructed to exhibit a convective air permeability of greater than about 0.1 cfm, preferably greater than about 1 cfm, and most preferably greater than about 10 cfm.

Moreover, it is important that this coated portion of the barrier layer exhibit a WVTR of from about 100 to about 50,000 gsm/day, more preferably from about 200 to about 25,000 gsm/day, even more preferably from about 300 to about 15,000 gsm/day, still more preferably from about 400 to abut 10,000 gsm/day, and most preferably from about 500 to about 5,000 gsm/day.

It has been found that when these features are combined, a disposable composite as disclosed herein is quite effective at providing the benefits deemed desirable when a consumer is looking for a breathable absorbent article for containment of body exudates, protective wear, or even personal hygiene care.

In preferred embodiments, the coated first region of the composites and absorbent articles of the present invention preferably has a dynamic liquid impact value of less than or equal to about 60 gsm, more preferably of less than or equal to about 40 gsm, even more preferably of less than or equal to about 20 gsm, and most preferably of less than or equal to about 7 gsm. In contrast, the second region preferably has a dynamic liquid impact value of greater than about 70 gsm.

In other preferred embodiments, the coated first region exhibits a barrier property that is measured by the Hydrohead Pressure Test that is described below. The hydrohead value of the first region that is coated with the barrier coating should be higher than that of a second or any additional regions of the same component on which no barrier coating is present. Preferably, this difference in hydrohead value between the barrier coated first region and the non-coated second region of the same component is at least about 1 mbar, more preferably at least about 5 mbars, and even more preferably at least about 10 mbars. The barrier coating preferably imparts an overall liquid resistance to the absorbent article (excluding the absorbent core and any tissue layers) of the present invention such that the coated first region of the barrier layer exhibits a hydrohead value of at least about 60 mbar, preferably at least about 70 mbar, more preferably at least about 80 mbar, and most preferably at least about 90 mbar.

The hydrohead value of the coated first region of the barrier layer may be affected if the barrier layer further comprises a fibrous web. Hydrohead values of such a fibrous web barrier layer would increase with finer fiber diameter, higher fiber density, higher basis weight, or combinations thereof. Suitable fibrous web on which the barrier coating may be disposed typically has a basis weight of at least about 2 gsm, preferably from about 5 to about 100 gsm, more preferably from about 10 to about 75 gsm, and most preferably from about 15 to about 55 gsm.

Without being limited by theory, convective transport capacity is different from diffusive transport capacity. The convective (i.e., both forced and free) transport is driven by a gas or air pressure differential and is typically at a much higher transport rate than diffusive transport, which is driven by random molecular movements. A typical example of diffusive transport includes the moisture migration through the pores of a microporous film such as those known in the art as the backsheet materials, or through the molecular structure of a nonporous monolithic film such as that made from Hytrel® (available from DuPont, Wilmington, Del.). Convective transport, on the other hand, is directed by the air pressure differential between the inside and the outside of the article. Though the local pressure (i.e., the local pressure within the space between the article and the wearer) and the pressure of the environment (i.e., outside the article) are substantially the same, small changes in the local pressure may cause convective air flow, typically through the gaps between the wearer and the article. Factors that may lead to convective transport include, but are not limited to, movements by the wearer, small pressure and/or temperature differential between the local and the outside environment, and the like.

With the advances made to absorbent articles, using elastic materials and elastic components, the absorbent articles now provide a tighter seal (i.e., fewer gaps) against the wearer's body to minimize fluid leakage to the outside. Consequently, the convective vapor flow through the gaps is substantially reduced, leading to a humid and hot local environment in the space between the article and the wearer. While absorbent cores are typically air permeable, the air permeability typically is reduced when the cores absorb liquid (i.e., become loaded). This air permeability is significantly affected further when microporous film backsheets are included in an article. The loaded cores can be vented (i.e., made air permeable) relatively easily, typically by venting means. Alternatively, openness of the core structures can be achieved by selecting particular arrangements of permeable materials.

These vented or open-structured cores generally require a leakage protection component, which is typically a microporous film backsheet or a relatively thick nonwoven fabric that provides liquid impermeability and leakage protection. These liquid impermeable components, however, tend to drastically reduce the air permeability of the overall absorbent article such that the convective air permeability of such components is virtually undetectable. In contrast, the barrier layer of the present articles allows convective air flow through the layer itself and thus through the entire article.

Typically, the barrier layer is positioned between the absorbent core and the outer cover, preferably adjacent to the garment-facing side of the absorbent core. In certain embodiments, the barrier layer may even be a component of the core, e.g., acting as a dusting layer. The barrier layer may be of a unitary structure. Alternatively, the layer may be a composite structure, which comprises a plurality of individual regions of materials that are joined or operatively associated together. The individual regions of the barrier layer may be coextensive or non-coextensive, depending on the requirements of the absorbent article. The individual regions may be joined by attachment means such as those well known in the art.

For example, the regions may be secured together by a uniform continuous layer of adhesive, or an array of separate lines, spirals, or droplets or beads of adhesive. The adhesive may be applied continuously or intermittently. For example, each application of the adhesive spans the length of the barrier layer and is separated from one another by a selected distance. The adhesive is applied to tack the regions together for handling the webs in the assembly process. Preferably, the adhesive is applied to portions of the surface of the barrier layer, leaving sufficient open (i.e., free of adhesives) surface areas for air/vapor permeability. Alternatively, the adhesive may be applied to modify the liquid impermeability. Typically, the open or adhesive-free surface area is no less than about 50%, preferably no less than about 70%, more preferably no less than about 80%, and most preferably no less than about 90% of the total surface area of the barrier layer. Suitable adhesives are manufactured by H. B. Fuller Company of St. Paul, Minn. and marketed as HL-1258 and by Ato-Findley Inc. of Milwaukee, Wis., under the trade designation H2031F.

Alternatively, the attachment means may comprise heat bonds, pressure bonds, ultrasonic bonds, mechanical bonds (via, for example, entanglements, cohesive forces, electric or static charges) or any other suitable attachment means or combinations of these attachment means as are known in the art.

Though the liquids are mainly absorbed by the absorbent core, the barrier layer provides additional leakage protection against errant liquids that are not absorbed by or are released from the absorbent core. Therefore, it is foreseeable that an additional absorbent layer may be included in the absorbent article of the present invention to act as a secondary absorbent or containment means to the core.

Liquid absorbency may vary, depending on the materials used in the absorbent core, the surface tension of the liquid being tested for absorbency, and the contact angle between the test liquid and the material.

The thickness and basis weight of the barrier layer may vary, depending on the materials used, the properties desired, the intended use, the construction, and the like. For example, thickness and/or basis weight may affect the diffusive breathability and/or the convective air permeability between the interior of an article and the outside, the absorbency and/or leakage protection of the article, the fit of the article to the wearer's body, the wearer's comfort, and like effects that typically relate to thickness of a structure. Typically, the barrier layer of the present invention intended for use in an absorbent article has a thickness of less than about 1.5 mm, preferably less than about 1.2 mm, and more preferably less than about 1.0 mm. The thickness of the barrier layer suitable for use in an absorbent article should also have a minimal thickness greater than about 0.1 mm, preferably greater than about 0.2 mm. Suitable materials for use herein are disclosed in U.S. Pat. Nos. 6,413,344, 6,521,555, and 6,488,801, all assigned to First Quality Nonwovens, Inc. (FQN). In particular, a 20 gsm meltblown from FQN is preferred for use herein.

The barrier coating and hence the first region is "substantially impermeable" to liquids, including water, breast milk, urine, menses, and other bodily fluids. The term "substantially impermeable" means that the barrier coating exhibits a resistance to liquid penetration but does not necessarily eliminate liquid wet through. In other words, it is possible for liquid to penetrate and flow through the barrier coating under normal wear conditions, such as under impact force, high applied pressure, or under sustained (i.e., continuously applied) pressure for a period of time. For example, when the first region of the barrier layer is positioned adjacent to the region of the absorbent core that is typically loaded with liquid upon insult, it provides additional protection against wet-through, particularly when the liquid loading level is high and/or the loaded absorbent core is under a sudden, high impact force or a sustained force/pressure.

This added wet-through protection is especially beneficial in diapers, training pants, pull-on diapers, or adult incontinence products, for which the liquid loading level can be fairly high (in comparison to feminine hygiene products) and the probability of sudden impact or sustained pressure (e.g., when babies or incontinent adults fall, sit down, roll, sleep) is also high. The barrier layer of the presently claimed absorbent articles and composites proves beneficial when the absorbent core is subjected to gushes of liquids. The resistance to liquid wet through provided by the barrier coating serves to temporarily slow down the gushes of liquids, possibly pooling the liquids at the interface between the absorbent core and the barrier coating. The slowed flow and pooling provide the additional time for the absorbent core to acquire and distribute the liquids to other regions of the core beyond the point of insult. Consequently, the absorbent core may achieve its full absorbent capacity.

Figure 2:
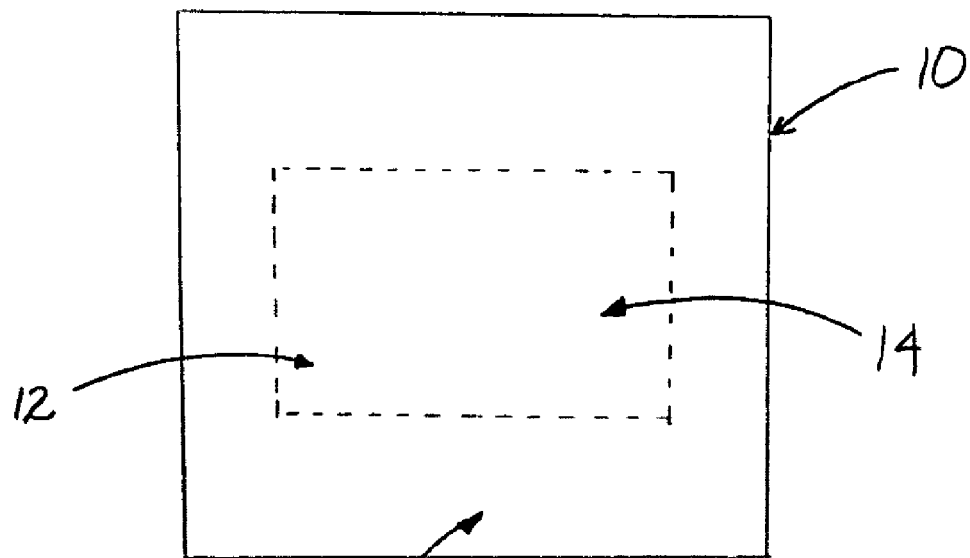
FIG. 2 is a top plan view of a composite of the present invention.

The function of the barrier layer component of the present invention can be more clearly understood by referring to the following illustrative figures. FIG. 2 shows a plan view of a composite of the article of the present invention. The barrier layer 10 comprises a first region 14, which coincides with the barrier coating 12 and a second region 16, which is uncoated.

As indicated in earlier discussion, the barrier coated first region is typically placed on the barrier layer in the area which is most prone to insult by the wearer's bodily exudates (in the case of a diaper or feminine care product) or in the area which is most likely to come in contact with wetness (in the case of other disposable garments).

Figure 3:
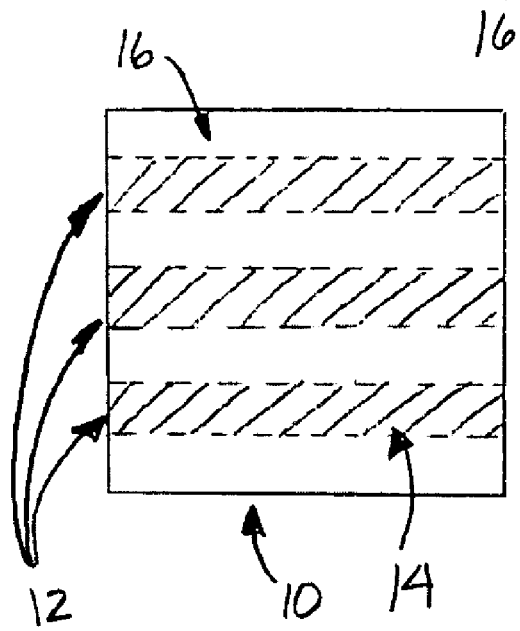
FIG. 3 is a top plan view of a striped barrier coated composite of the present invention.

Various arrangements of the barrier coating in the barrier layer are shown in FIG. 3. In FIG. 3, the first region 14 is striped in relationship to the second region within the barrier layer such that multiple regions are formed. In FIG. 3, the barrier coating 12 is disposed in a first region in the form of a discrete stripe shape, which could likewise be in alternative shapes or discontinuous patterns, such as circles, ellipses, squares, animated characters, etc.

In preferred embodiments of the present invention, at least a portion of the barrier coating is positioned adjacent to the garment-facing side of the absorbent core. In one embodiment, the barrier coating may extend through substantially the entire portion of the absorbent core or the barrier coating may be stripes or patches that extend to portions of the absorbent core. In another embodiment, the barrier layer may extend beyond the outer edges of the absorbent core or only through the length and width of the central portion of the absorbent core. Configurations in which the barrier coating has at least the same length and width of the absorbent core are highly preferred. An even more preferred embodiment includes a barrier coating on the region of the barrier layer that is most prone to insult by a wearer (in the case of an absorbent article).

Moreover, the barrier coated first region may cover the expanse of at least about 5% of the entire area of the barrier layer. More preferably, the barrier coating is disposed on at least about 15% of the entire area. Even more preferably, the barrier coating is disposed on at least about 25% of the entire area. Most preferably, however, the barrier coating covers at least about 50% of the entire area of the barrier layer.

Additionally, irrespective of the amount of area that is covered by the barrier coating, the coating may be applied in a gradient in the cross direction, machine direction, or both. Likewise, the pattern formed by the barrier coating may be continuous or intermittent in form as discussed above with the stripes, dots, etc. along the width or length of the layer.

In order to provide the desired hydrohead value or the "barrier-like" property, the barrier coating comprises one or more materials that substantially closes or block the openings (as opposed to the full length) of the pores of the portion of the barrier layer onto which it is deposited. More specifically, the barrier coating comprises one or more materials selected from the group consisting of thermoplastic materials (such as hotmelt adhesives), solutions, emulsions, dispersions, and combinations thereof. For instance, suitable barrier coating comprises materials selected from the group consisting of microcrystalline waxes, stearyl behenates, sucrose fatty acids, polyisobutylenes, ethylene-vinyl acetate copolymer resins, polyethylene waxes, fatty alcohols, sucrose fatty acid esters, stearyl alcohol, sucrose hardened soy esters having an iodine value of less than 107 (preferably less than 90), natural alcohol still bottoms, wax esters (e.g., sorbitan wax ester, fatty-fatty wax ester, sucrose wax esters), aldol condensation products with melting points greater than 60° C., natural petroleum waxes, lube base stocks, ozokerite wax, synthetic petroleum waxes, beeswax, stearic acids, spermaceti, carnauba wax, hydrogenated soybean oil, unhydrogenated soybean oil, corn oil, palm oil, coconut oil, castor oil, linseed oil, safflower oil, sunflower oil, rapeseed oil, silicones, xanthan gum, gum arabic, celluloses, chemical and enzyme-modified starches, petrolatums, mineral oils, vinyl copolymers, vinyl emulsifiers, sorbitol, propylene glycol, glycerine, solid esters, and combinations thereof. More preferably, the barrier coating comprises one or more materials selected from the group consisting of microcrystalline waxes, thermoplastic materials, stearyl behenates, stearyl alcohols, silicones, silicone waxes, and combinations thereof. Even more preferably, the barrier coating comprises one or more materials selected from the group consisting of microcrystalline waxes, hotmelt adhesives, and combinations thereof. Suitable hotmelt adhesives include H. B. Fuller's HL-1258.

Most preferred as a barrier coating is a microcrystalline wax. A suitable wax for use in the present invention is Multiwax W-835, which is commercially available from The C.P. Hall Company. This material is a highly refined, high molecular weight microcrystalline petroleum wax that consists of saturated branched and cyclic non-polar hydrocarbons.

In certain embodiments, it is preferred that such barrier coating materials are disposed onto a first region of the barrier layer such that the basis weight of the coated first region ranges from about 5 to about 200 gsm, more preferably from about 10 to about 100 gsm, even more preferably from about 15 to about 75 gsm, and most preferably from about 25 to about 50 gsm.

It is desirable that the barrier coating wet the barrier layer in the first region even when the layer itself is modified with other treatments (e.g., polypropylene web treated with plasma, a hydrophobic surface coating, etc.)

Other Components

In order to optimize the absorbent article disclosed herein, it may be desirable to ensure that it includes one or more of the belowmentioned features.

The absorbent article may also include a fastening system 40. The fastening system 40 preferably maintains the first waist region 36 and the second waist region 38 in a configuration so as to provide lateral tensions about the circumference of the absorbent article to hold the absorbent article on the wearer. The fastening system preferably comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594, 4,662,875, 4,846,815, 4,894,060, 4,946,527, 5,151,092, and 5,221,274. An exemplary interlocking fastening system is disclosed in U.S. Pat. No. 6,432,098. The fastening system may also provide a means for holding the article in a disposal configuration as disclosed in U.S. Pat. No. 4,963,140. The fastening system may also include primary and secondary fastening systems, as disclosed in U.S. Pat. No. 4,699,622 or to improve fit as disclosed in U.S. Pat. Nos. 5,242,436, 5,499,978, 5,507,736, and 5,591,152.

The absorbent article may also comprise side panels. The side panels may be elastic or extensible to provide a more comfortable and contouring fit by initially conformably fitting the diaper to the wearer and sustaining this fit throughout the time of wear well past when the diaper has been loaded with exudates since the elasticized side panels allow the sides of the diaper to expand and contract. The side panels 30 may also provide more effective application of the diaper because even if the diaperer pulls one elasticized side panel farther than the other during application, the diaper will "self-adjust" during wear.

While the diaper of the present invention preferably has the side panels disposed in the second waist region, the diaper may be provided with side panels disposed in the first waist region or in both the first waist region and the second waist region. The side panels 30 may be constructed in any suitable configurations. Examples of diapers with elasticized side panels are disclosed in U.S. Pat. Nos. 4,857,067, 4,381,781, 4,938,753, 5,151,092, 5,221,274, 5,669,897, and 6,004,306.

In a preferred embodiment, the absorbent article further comprises at least a first cuff for providing improved containment of liquids and other body exudates; an elastic waist feature that provides improved fit and containment; and a fastening system which forms a side closure which maintains the first waist region and the second waist region in an overlapping configuration such that lateral tensions are maintained around the circumference of the absorbent article to maintain the absorbent article on the wearer. The absorbent article may also comprise elasticized side panels (not shown) in the waist regions and to provide an elastically extensible feature that provides a more comfortable and contouring fit and more effective application of the absorbent article.

The elasticized leg cuffs 32 can be constructed in a number of different configurations, including those described in U.S. Pat. Nos. 3,860,003, 4,636,207, 4,695,278, 4,704,115, 4,795,454, 4,900,317, 4,909,803 (Reissued as U.S. RE 34920), 5,085,654, 5,492,751, 6,476,288 and SIR H1630.

For example, the absorbent article may include one ore more first cuffs that provide improved containment of liquids and other body exudates. First cuffs may also be referred to as outer leg cuff, leg bands, side flaps, leg cuffs or elastic cuffs. U.S. Pat. No. 3,860,003 describes a disposable diaper which provides a contractible leg opening having a side flap and one or more elastic members to provide an elasticized leg cuff.

Additionally, an absorbent article of the present invention may include one or more second cuffs that also provide improved containment of liquids and other body exudates. Second cuffs may also be referred to as barrier leg cuffs, inner leg cuffs or "stand-up" elasticized flaps. U.S. Pat. Nos. 4,808,178 and 4,909,803 describe disposable diapers having "stand-up" elasticized flaps that improve the containment of the leg regions.

First cuff and second cuff may both be provided by way of a dual cuff, as exampled in U.S. Pat. Nos. 4,695,278 and 4,795,454. Additional cuffs may be provided in an article of the present invention as detailed in US Statutory Invention Registration H1630, which published Jan. 7, 1997.

Another component that may be included in the articles or composites of the present invention is a hydrophobic surface coating as disclosed in copending U.S. provisional application Ser. No. 60/543,785 (P&G Case 9528P). This hydrophobic surface coating may be paired with the barrier coating of the present invention on the barrier layer or may be disposed adjacent to one or more additional components of the absorbent articles or composites of the present invention. For instance, this hydrophobic surface coating may be disposed on an interior surface of one or more leg cuffs, waist portions, or other areas of the absorbent article.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. Nos. 5,514,121, 5,171,236, 5,397,318, 5,540,671, 6,168,584, 5,306,266, 5,997,520. Examples of compartments or voids are disclosed in U.S. Pat. Nos. 4,968,312, 4,990,147, 5,062,840, 5,269,755. Examples of suitable transverse barriers are described in U.S. Pat. No. 5,554,142, PCT Patent WO 94/14395, and U.S. Pat. No. 5,653,703. Examples of other structures especially suitable for management of low viscosity feces are disclosed in U.S. Pat. Nos. 5,941,864, 5,977,430, and 6,013,063.

All documents cited in the Detailed Description of the Invention are, in relevant part, incorporated herein by reference; the citation of any document is not to be construed as an admission that it is prior art with respect to the present invention.

Test Methods

Convective Air Permeability

The convective air permeability is determined by measuring the time in which a standard volume of air is drawn through a test specimen at a constant pressure and temperature. This test is particularly suited to materials having relatively high permeability to gases, such as nonwovens, apertured films and the like.

A TexTest FX3300 air permeability tester is used. The test method conforms to ASTM D737. The test is operated in a laboratory environment typically about 23±2° C. and about 30%±15% relative humidity. The test specimen has to be conditioned for at least 2 hrs. The test pressure is 125 Pascals and the test area is 38 cm². In this test, the instrument creates a constant differential pressure across the sample which draws air through the sample. The rate of air flow through the sample is measured in cfm. For each sample, five replicates should be run, and the averaged result is reported as the air permeability value.

Hydrostatic Head (Hydrohead) Pressure Test

The hydrohead pressure or hydrohead value is a measure of the liquid barrier property (or liquid impermeability) of a material. Specifically, the test described herein measures the hydrostatic pressure the material will support when water penetration occurs.

The TexTest Hydrostatic Head Tester FX3000 (available from Advanced Testing Instruments, Corp., Spartanburg, S.C.) is used. The test method conforms to Edana 120.1-18 (also INDA IST 80.6). For this test, gradually increasing pressure is applied to a defined sample portion until water penetrates through the sample.

The test is conducted in a laboratory environment typically about 73° F.±2.0° F. (23° C.±2° C.) and a relative humidity of about 30%±15%. The sample is clamped over the top of the column fixture, using an appropriate gasketing material (o-ring style) to prevent side leakage during testing. In order to determine the hydrohead pressure of the barrier coated first region of the barrier layer, a sample of the barrier layer is oriented such that the barrier coated region of the barrier layer faces the water column during the test. The area of water contact with the sample is equal to the cross sectional area of the water column, which equals 28 cm² or 100 cm². Similarly, the hydrohead pressure of the uncoated second region is determined by orienting this region facing the water column during the test.

In either instance, water is pumped into the water column at a rate to achieve a pressure increase of 3 mbar/min or 60 mbar/min. Thus, the sample is subjected to a steadily increasing water pressure on one surface. When water penetration appears on three locations on the other surface of the sample, the pressure at which the third penetration occurs is recorded. If water immediately penetrates the sample (i.e., the sample provided no resistance), a zero reading is recorded. For each material, five specimens are tested and the results are averaged and reported in mbars.

Dynamic Liquid Impact Value

The objective of the test method is to mimic the dynamic load/area (energy) that a baby will impart to a saturated core/backsheet structure when the baby abruptly goes from a standing to a sitting position. Dynamic liquid impact (g/m²) is calculated based on the impact energy an average 20 lb. baby will impart to a saturated diaper if he/she "falls" onto it from a standing position. The baby was modeled as two rigid links of known mass and length. The theory was made that the links "fall" from rest, with the impact area being the region under the diaper. This works out to be approximately 20 Joules (14.75 ft-lb.) over an average baby "seat" area 0.0087 m² (~13.5 in²) or 2300 J/m². In order to conduct this method, a dynamic liquid impact tester is required. This tester is depicted in FIG. 4.

Test Equipment and Supplies
1. Bottom plate 214 (305 mm×305 mm steel plate, 25.5 mm thick);
2. Impact disc 212 (white nylon (McMaster Carr #8538K34) 61 mm dia., 12.7 mm thick) with a 5 mm pin 220 inserted in the center);
3. Lexan sample plate 206 (153 mm×153 mm Lexan plastic block, 19 mm thick, which includes a circular cut out area for insertion of the guide tube 204;
4. Lexan guide tube 204 (Lexan plastic tube of 3 mm thickness and an inner diameter of 64 mm;
5. Impact weight 209 (3370 g+5 g stainless steel cylinder, 149 mm long and a diameter that is lightly less than that of the guide tube 204 to allow it to move freely in the vertical direction therein);
6. Vacuum cup 208;
7. Impact pad 222 (Silicon Rubber Sheet, 50 A durometer hardness, 6"×6"×⅜" thick;
8. Filter paper (Whatman #4 Filter Paper, 1004-070, 70 mm diameter, VWR catalog # 28460-041);
9. Liquid used to load filter paper (0.9% Sodium Chloride solution);
10. 10 ml plastic syringe or equivalent;
11. Starrett rules (Starrett 150 mm Rule, Starrett 300 mm Rule); and
12. Control material (125 mm×125 mm Exxaire Exxon XBF 100W).

Figure 4:
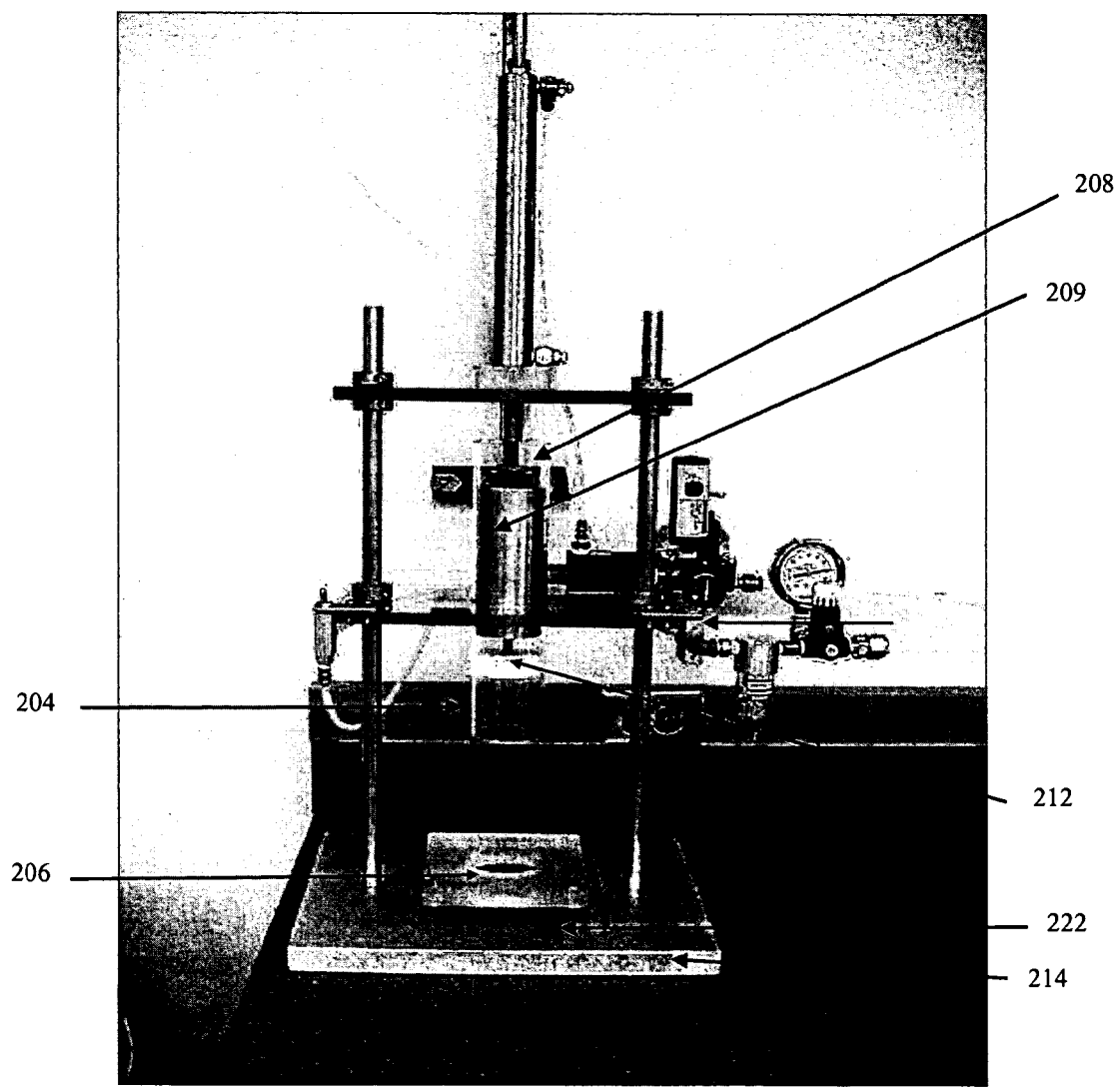
FIG. 4 is a front view of the dynamic liquid impact tester that is used relative to the present invention.

Parts 1-7 are assembled as shown in FIG. 4. The distance between the bottom of the impact weight 209 to the bottom of the impact pad 212 is set to 40 mm±3.0 mm.

It is important to note that this method uses two filter papers to record the moisture transferred through the test sample. It also requires a stack of five filter papers to carry the wetting medium.

The two "receiving" filter papers are weighed to within ±0.1 mg and the mass is recorded. The stack of five filter papers need only be weighed to within ±0.01 g.

Test Steps
1. Place two pieces of 70 mm diameter filter paper on a balance accurate to 0.0001 gram. Record the filter paper's mass after about one minute or when balance reading stabilizes.
2. Place five pieces of 70 mm diameter filter paper onto a balance accurate to 0.01 gram. Assure a "dry" mass is 1.72 g+0.10 g.
3. Raise the bottommost portion of the impact weight to a height of 290 mm+2 mm from the top of the base plate.
4. Remove the Lexan sample plate and center the five filter papers on the impact pad, which is centered on the base plate.
5. Set two timers: set one for 2 minutes and set the other for 3 minutes. The 2-minute timer signals when to raise the impact weight. The 3-minute timer signals when to record the final weight of the two filter papers.
6. Draw 2.0 ml (+0.05 ml) of 0.9% NaCl solution into a calibrated syringe. Apply the NaCl solution to the five filter papers.
7. Place a 125 mm×125 mm section of test material on the saturated filter papers assuring the wet filter papers remain in the "stacked" position. The side of the material that would be the outside of the absorbent article needs to face up. (Note—The time between placing the test material on the wet filter papers and releasing the impact weight must be minimized. Assure all activities, i.e., setting timers, weighing the filter paper, are completed)
8. Place the Lexan sample plate over the test material while insuring that the aperture contained therein is aligned with the bottom of impact weight.
9. Using tweezers/tongs place the two receiving, weighed filter papers over the test material.
10. Release the impact weight and start both timers.
11. When the 2-minute timer signals, raise the impact weight and secure it.
12. Promptly transfer the two filter papers (using tweezers/tongs) to the balance valid to 0.0001 g.
13. When the 3-minute timer signals, record the filter paper's mass to the nearest 0.0001 g.
14. Remove the Lexan sample plate, the test material and wet filter paper from the LIT. Dry the rubber pad and the Lexan sample plate with a Bounty towel (or equivalent). Repeat steps 1-2 and 5-14 for next test.

Calculation of Dynamic Liquid Impact Value

"Dynamic" Liquid Impact Value=Filter Mass Change (grams)/Impact Area($m^2$)Impact Area=0.002932 $m^2$ Sample Calculation:

| Filter Dry Mass (grams) | Filter Wet Mass (grams) | Filter Mass Change (grams) | Dynamic Impact Value ($g/m^2$) |
|---|---|---|---|
| 0.3465 | 0.3815 | 0.0350 | 11.9 |

0.0350 g/0.002932 $m^2$=11.9372 $g/m^2$ (or gsm)

Water Vapor Transmission Rate

The water vapor transmission rate is a measure of the rate at which water vapor flows through flexible barrier materials. Accordingly, INDA IST 70.4(01), which is the Standard Test Method for Water Vapor Transmission Rates of 500 to 100,000 gsm/day Through Nonwoven Fabrics and Plastic Barriers, is used to determine the WVTR of the entire absorbent article's thickness.

EXAMPLES

Example 1

A composite according to the present invention is prepared.
A microcrystalline wax barrier coating (commercially available from The C. P. Hall Company under the tradename Witco W-835) is applied to a 20 gsm meltblown from First Quality Nonwovens, Inc. which measures 142 mm×132 mm using a Nordson hotmelt slot coater at an add-on rate of 33 gsm. This coating extends across the width of the layer covering about 25% of area of the barrier layer.

Example 2

A composite according to the present invention is prepared.
The composite of Example 1 is modified to further include a hydrophobic surface coating that is added to the meltblown prior to the addition of the wax barrier coating. This hydrophobic surface coating is an aqueous mixture of vinyl terminated polydimethyl siloxane and methylhydrogen polydimethyl siloxane in a 30:1 ratio in order that approximately 0.1 gsm of the aqueous silicone mixture (which includes a transition metal catalyst) is deposited via a kiss roll onto the meltblown in at least the first region. The meltblown barrier layer is dried at 120° C. for 1-3 minutes. Thereafter, the barrier coating of Example 1 is applied as detailed above.

Example 3

An absorbent article according to the present invention is prepared.
A multi-piece diaper is constructed with a barrier layer with a barrier coating that is longer and wider than the absorbent core, extending up to the gasketing leg cuff portion and 10 mm beyond each end of the absorbent core. The composite of Example 1 or 2 is placed between the absorbent core and the outer cover with the barrier coating facing the core in a diaper as detailed in any one of U.S. Pat. Nos. 3,860,003, 4,636,207, 4,695,278, 4,704,115, 4,795,454, 4,900,317, 4,909,803 (Reissued as U.S. RE 34920), 5,085,654, 5,492,751, 6,476,288, 6,627,787, 5,507,760, 5,609,587, 5,635,191, 5,643,588, 6,118,041 and SIR H1630.

Example 4

An absorbent article of the present invention is prepared.
The composite of Example 1 or 2 is modified to include a 22 gsm Interlake tissue (absorbent layer) on the surface facing the outer cover of a diaper prepared as detailed in Example 3.

Example 5

A pull-on type absorbent article of the present invention is prepared.
A pull-on type absorbent article as detailed in any one of U.S. Pat. Nos. 5,246,433, 5,769,838, 5,899,895, 5,899,896, and 6,120,487 is modified to include the composite of Example 1 or 2.

Example 6

A pull-on type absorbent article of the present invention is prepared.
The composite of Example 1 or 2 is modified to include a 22 gsm Interlake tissue (absorbent layer) on the surface of the composite which is placed facing the outer cover of the pull-on article of Example 5.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A disposable absorbent article comprising:
   a. a liquid permeable topsheet;

b. a liquid impervious outer cover;
c. an absorbent core disposed between said topsheet and outer cover; and
d. a barrier layer comprising a fibrous sheet having a first side and an opposing second side, said first side having a total surface area, the barrier layer being disposed between said core and outer cover, wherein said barrier layer further comprises:
  1) a first region of the fibrous sheet having a first region surface area on said first side, the first region surface area forming a portion of the total surface area, wherein the first region surface area is smaller than the total surface area, the first region having a non-fibrous coating deposited thereon, the coating being disposed on the fibrous sheet between the absorbent core and the outer cover: and
  2) a second region of the fibrous sheet adjacent said first region of the fibrous sheet, having a second region surface area on said first side, the second region surface area forming a portion of the total surface area, wherein the second region surface area is smaller than the total surface area;
  wherein the non-fibrous coating comprises one or more materials selected from the group consisting of microcrystalline waxes, stearyl behanates, sucrose fatty acids, polyethylene waxes, fatty alcohols, sucrose fatty esters, stearyl alcohol, sucrose hardened soy esters having an iodine value of less than 107, natural alcohol still bottoms, wax esters, aldol condensation products with melting points greater than 60° C., natural petrolatum waxes, ozokerite wax, synthetic petroleum waxes, beeswax, stearic acids, carnauba wax, hydrogenated soybean oil, unhydrogenated soybean oil, corn oil, palm oil, coconut oil, castor oil, linseed oil, safflower oil, sunflower oil, rapeseed oil, silicones, silicone waxes, xantham gum, gum arabic, petrolatums, mineral oils, vinyl copolymers, vinyl emulsifiers, sorbitol, propylene glycol, glycerine solid esters and combinations thereof;
  wherein the non-fibrous coating inhibits the flow of a liquid in the first region of the fibrous sheet as compared to the flow of the liquid in the second region of the fibrous sheet;
  wherein said first region of the fibrous sheet with the non-fibrous coating exhibits a water vapor transmission rate (WVTR) of from about 100 to about 50,000 gsm/day and a convective air permeability of at least about 0.01 cfm;
  wherein said second region of the fibrous sheet is substantially free of the non-fibrous coating and exhibits a convective air permeability of at least about 0.1 cfm; and
  wherein the non-fibrous coating is deposited onto the first region of the fibrous sheet via a mechanism selected from the group consisting of spraying, dipping, brushing, coating, printing, slot-coating, and combinations thereof.

2. The article of claim 1 wherein said barrier layer further comprises an absorbent layer.

3. The article of claim 1 wherein the hydrohead value difference between the first region of the fibrous sheet and the second region of the fibrous sheet is greater than about 1 mbar.

4. The article of claim 1 wherein said first region of the fibrous sheet exhibits a dynamic liquid impact value of less than or equal to about 60 gsm.

5. The article of claim 2 wherein said first region of the fibrous sheet exhibits a dynamic liquid impact value of less than or equal to about 60 gsm.

6. The article of claim 1 wherein said barrier layer is disposed adjacent to one or more of the topsheet, core, and outer cover.

7. The article of claim 1 wherein said article further comprises an additional component that is contacted with a hydrophobic surface coating.

8. The article of claim 1 wherein said barrier layer comprises a nonwoven substrate having a basis weight of less than about 45 gsm.

9. A disposable composite comprising a topsheet, an outer cover, an absorbent core disposed between the topsheet and the outer cover, and at least one barrier layer disposed between the absorbent core and the outer cover, the barrier layer comprising a fibrous sheet having a first side and an opposing second side, said first side having a total surface area, and further comprising:
  a. a first region of the fibrous sheet having a first region surface area on said first side, the first region surface area forming a portion of the total surface area, wherein the first region surface area is smaller than the total surface area, the first region having a non-fibrous coating deposited thereon, the coating being disposed on the fibrous sheet between the absorbent core and the outer cover; and
  b. a second region of the fibrous sheet, having a second region surface area on said first side, the second region surface area forming a portion of the total surface area, wherein the second region surface area is smaller than the total surface area;
  wherein the non-fibrous coating comprises one or more materials selected from the group consisting of microcrystalline waxes, stearyl behanates, sucrose fatty acids, polyethylene waxes, fatty alcohols, sucrose fatty esters, stearyl alcohol, sucrose hardened soy esters having an iodine value of less than 107, natural alcohol still bottoms, wax esters, aldol condensation products with melting points greater than 60° C., natural petrolatum waxes, ozokerite wax, synthetic petroleum waxes, beeswax, stearic acids, carnauba wax, hydrogenated soybean oil, unhydrogenated soybean oil, corn oil, palm oil, coconut oil, castor oil, linseed oil, safflower oil, sunflower oil, rapeseed oil, silicones, silicone waxes, xantham gum, gum arabic, petrolatums, mineral oils, vinyl copolymers, vinyl emulsifiers, sorbitol, propylene glycol, glycerine solid esters and combinations thereof;
  wherein the non-fibrous coating inhibits the flow of a liquid in the first region of the fibrous sheet as compared to the flow of the liquid in the second region of the fibrous sheet;
  wherein said first region of the fibrous sheet exhibits a water vapor transmission rate (WVTR) of from about 100 to about 50,000 gsm/day and a convective air permeability of at least about 0.01 cfm;
  wherein said second region of the fibrous sheet is substantially free of the non-fibrous coating and exhibits a convective air permeability of at least about 0.1 cfm; and
  wherein the non-fibrous coating is deposited onto the first region surface via a mechanism selected from the group consisting of spraying, dipping, brushing, coating, printing, slot-coating, and combinations thereof.

10. The composite of claim 9 wherein said barrier layer comprises a nonwoven substrate having a basis weight of less than about 45 gsm.

11. The composite of claim 9 wherein said composite comprises an absorbent layer.

12. The composite of claim 9 wherein the hydrohead value difference between the first region of the fibrous sheet and the second region of the fibrous sheet is greater than about 1 mbar.

13. The composite of claim 9 wherein said first region of the fibrous sheet exhibits a dynamic liquid impact value of less than or equal to about 60 gsm.

14. The composite of claim 11 wherein said first region of the fibrous sheet exhibits a dynamic liquid impact value of less than or equal to about 60 gsm.

15. A disposable absorbent article wherein said article comprises the composite of claim 9.

16. The article of claim 15 wherein said article is selected from the group consisting of diapers, training pants, adult incontinence products, feminine care napkins, bibs, care mats, breast pads, wound dressing products, and combinations thereof.

17. A disposable absorbent article comprising:
   a. a liquid permeable topsheet;
   b. a liquid impervious outer cover;
   c. an absorbent core disposed between said topsheet and outer cover; and
   d. a barrier layer comprising a fibrous sheet having a first side and an opposing second side, said first side having a total surface area, the barrier layer being disposed between said core and outer cover, wherein said barrier layer further comprises:
      1) a first region of the fibrous sheet having a first region surface area on said first side, the first region surface area forming a portion of the total surface area, wherein the first region surface area is smaller than the total surface area, the first region having a non-fibrous coating comprising a wax deposited thereon, the coating being disposed on the fibrous sheet between the absorbent core and the outer cover; and
      2) a second region of the fibrous sheet adjacent said first region of the fibrous sheet, having a second region surface area on said first side, the second region surface area forming a portion of the total surface area, wherein the second region surface area is smaller than the total surface area;
      wherein the non-fibrous coating inhibits the flow of a liquid in the first region of the fibrous sheet as compared to the flow of the liquid in the second region of the fibrous sheet;
      wherein said first region of the fibrous sheet with the non-fibrous coating exhibits a water vapor transmission rate (WVTR) of from about 100 to about 50,000 gsm/day and a convective air permeability of at least about 0.01 cfm;
      wherein said second region of the fibrous sheet is substantially free of the non-fibrous coating and exhibits a convective air permeability of at least about 0.1 cfm; and
      wherein the non-fibrous coating is deposited onto the first region of the fibrous sheet via a mechanism selected from the group consisting of spraying, dipping, brushing, coating, printing, slot-coating, and combinations thereof.

* * * * *